United States Patent [19]

Bakalyar

[11] Patent Number: 4,506,558
[45] Date of Patent: Mar. 26, 1985

[54] INJECTOR WITH MINIMAL FLOW-INTERRUPT TRANSIENT

[75] Inventor: Stephen R. Bakalyar, Sebastopol, Calif.

[73] Assignee: Rheodyne Incorporated, Berkeley, Calif.

[21] Appl. No.: 471,753

[22] Filed: Mar. 3, 1983

[51] Int. Cl.³ ............................................. G01N 1/10
[52] U.S. Cl. ............................. 73/863.72; 73/864.83
[58] Field of Search .......... 73/864.84, 864.83, 863.72, 73/863.73

[56] References Cited

U.S. PATENT DOCUMENTS

| | | | |
|---|---|---|---|
| 3,393,551 | 7/1968 | Todd et al. | 73/864.83 X |
| 3,630,371 | 12/1971 | Hedina | 73/864.83 X |
| 3,961,534 | 6/1976 | Gundelfinger | 73/864.84 |
| 4,068,528 | 1/1978 | Gundelfinger | 73/864.84 |
| 4,182,184 | 1/1980 | Bakalyar et al. | 73/864.87 |
| 4,393,726 | 7/1983 | Tomm et al. | 73/864.84 |

*Primary Examiner*—S. Clement Swisher
*Assistant Examiner*—Tom Noland
*Attorney, Agent, or Firm*—Freilich, Hornbaker, Rosen & Fernandez

[57] ABSTRACT

An injector is described for injecting a sample at a high pressure into a chromatographic column, which avoids sample dilution that is characteristic of bypass loop injectors, and which also avoids significant flow interruption into the column that is characteristic of prior non-bypass injectors. The stator includes pump and column ports with openings (34a, 42a, FIG. 4) at the stator-rotor interface, where the openings are spaced by a small angle (m) of less than 10° from one another. In the load position, a channel (50) formed in the interface surface of the rotor, which connects the pump and column openings in the load position, extends away from the pump opening by an angle (n) which is many times greater than the angle between the pump and column openings. As a result, as the injector is turned toward the inject position, the channel (50) continues to connect the pump and column openings until the rotor is close to the inject position. As the inject position is approached (FIG. 8), the trailing edge (50t) of the channel passes beyond the pump openings (34a), while the leading edge (50f) of the channel connects to a sample opening (the channel is always connected to the column opening (42a). Thus, when the rotor is rapidly turned from load to inject positions, there is only a very brief interruption of liquid flow into the column.

9 Claims, 19 Drawing Figures

LOAD

INJECT

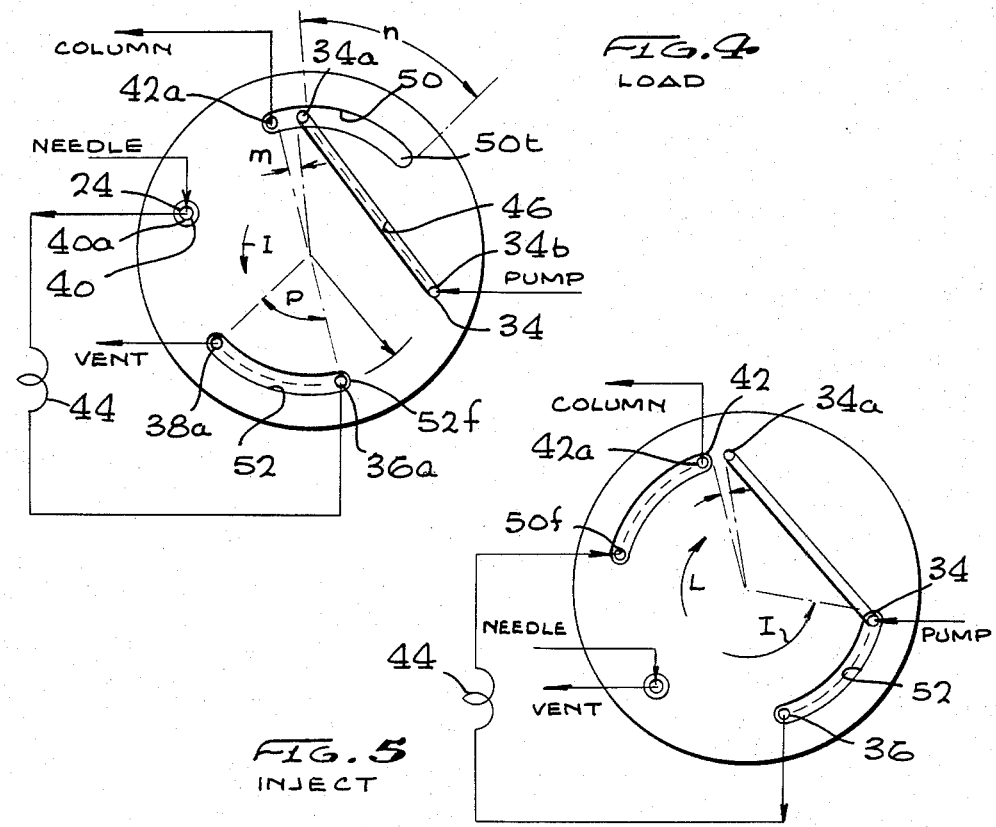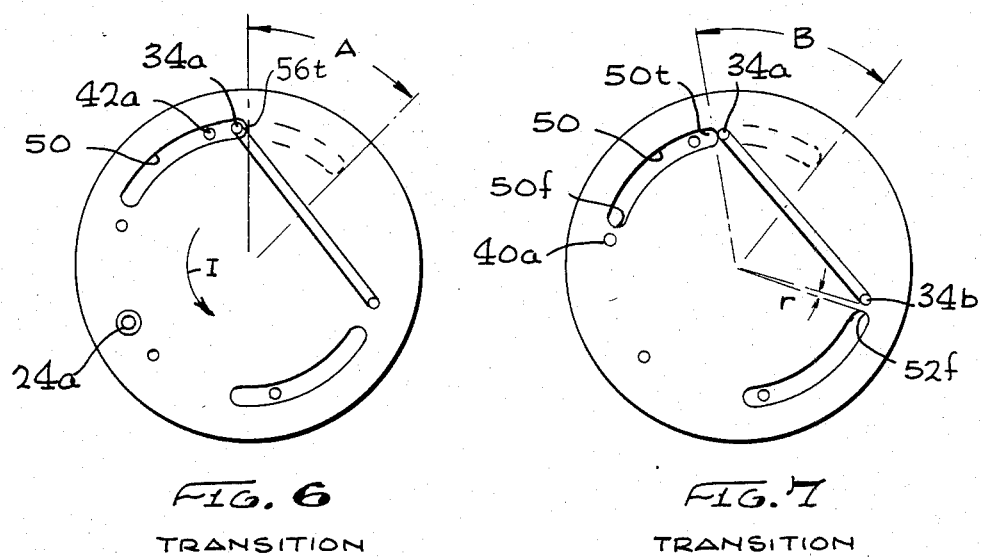

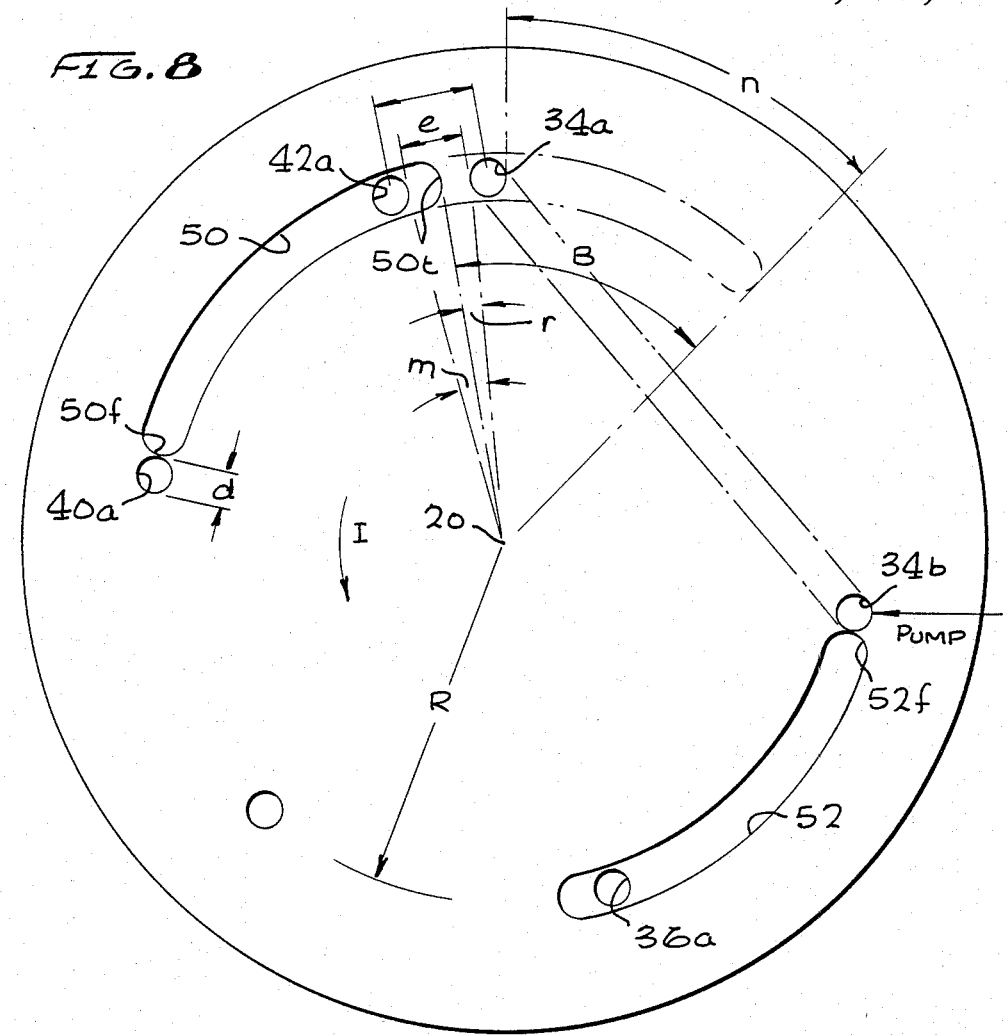
FIG. 8
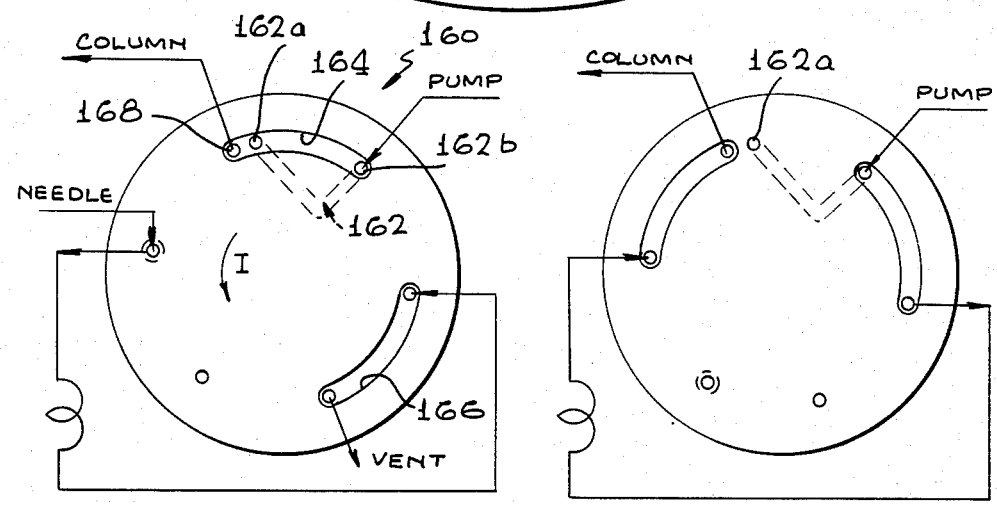
FIG. 9 LOAD
FIG. 10 INJECT

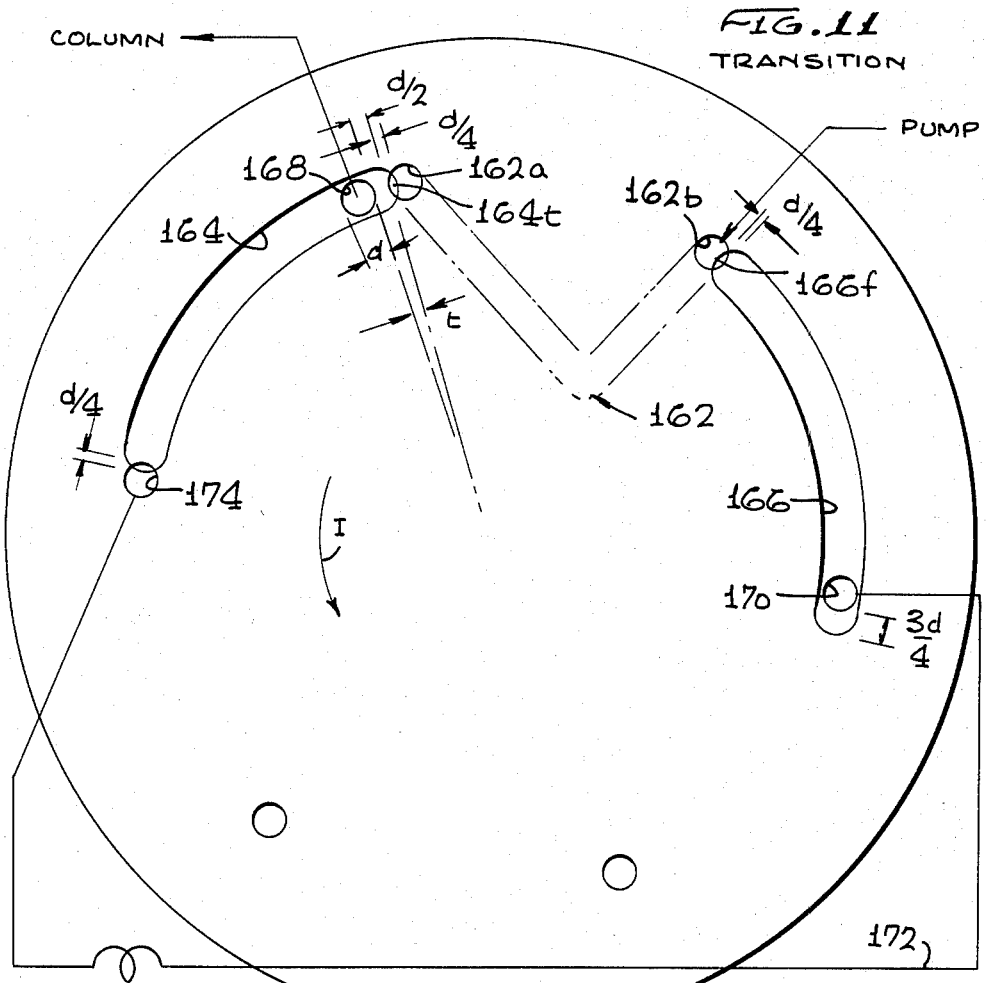
FIG. 11 TRANSITION
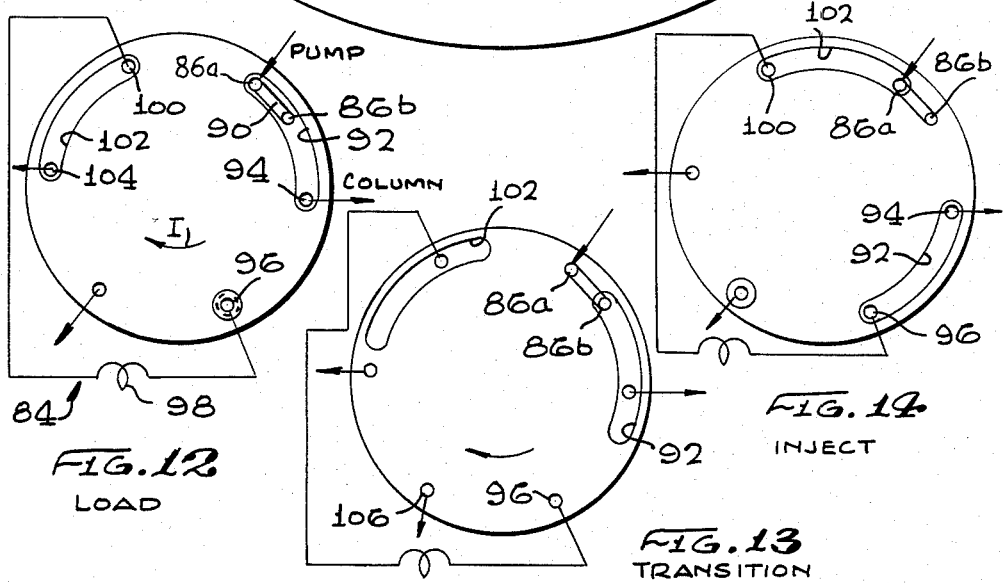
FIG. 12 LOAD
FIG. 13 TRANSITION
FIG. 14 INJECT

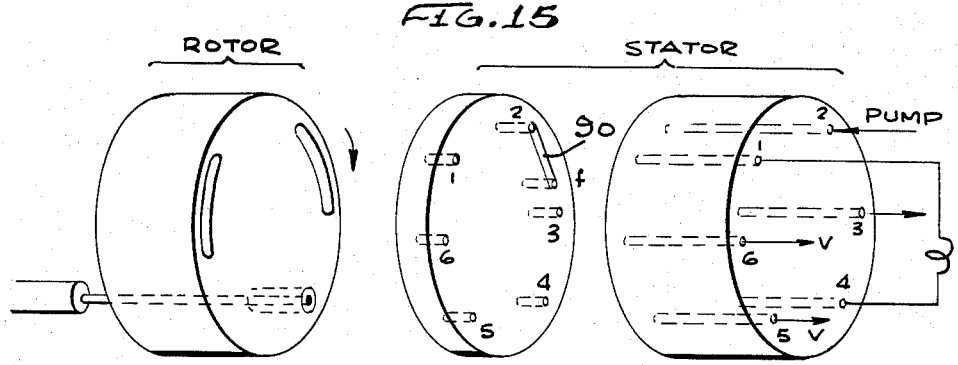
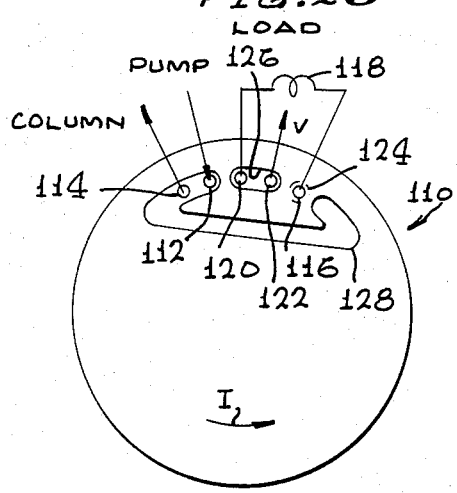
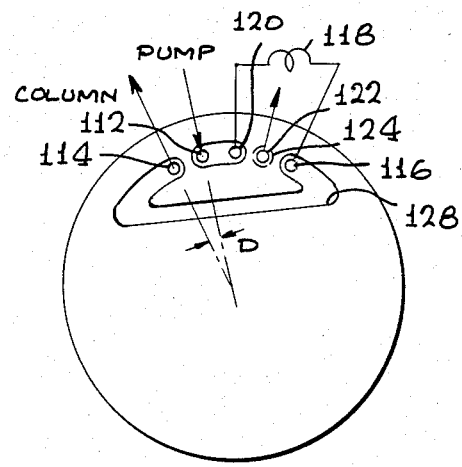
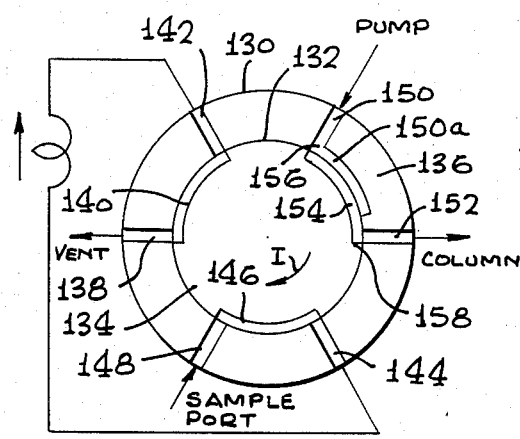
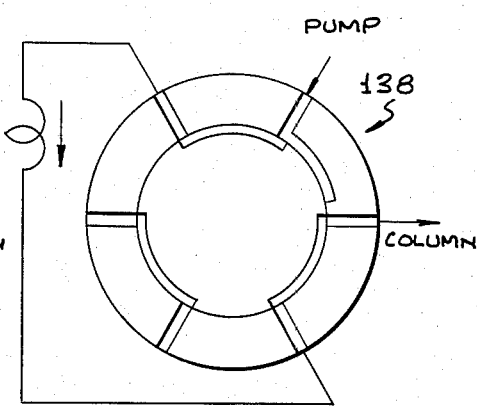

INJECTOR WITH MINIMAL FLOW-INTERRUPT TRANSIENT

BACKGROUND OF THE INVENTION

Injectors which are used to inject a small sample into a chromatographic column, have generally been either of two types. One type is an injector with a bypass conduit (bypass loop), such as described in U.S. Pat. No. 3,961,534 by Gundlefinger, wherein a mobile phase liquid (solvent) is always applied under pressure to the column port of the injector, and the sample is applied to the column by connecting a sample chamber (sample loop) to flow in parallel with the solvent. The streams from the bypass loop and sample loop are united before entering the column. Such parallel flow has the advantage of providing an uninterrupted flow into the column, but has the disadvantage that resolution and sensitivity are decreased because of dilution of the sample by the solvent. There is a possibility of major dilution if there is a particle or other partial obstruction in the sample loop.

Injectors are available without bypass loops, such as described in U.S. Pat. No. 4,182,184 by Bakalyar, wherein the solvent initially flows into the column, and this flow is terminated and sample flow into the column begins when a rotor is turned. Such non-bypass injectors have the advantage of avoiding dilution of the sample with solvent. However, they have the disadvantage that the interruption of flow can cause detector baseline noise and reduced column efficiency.

The interruption of flow occurs in non-bypass injectors, during a brief transition period while the rotor is turning between the load and inject positions. At the beginning of this invention period, the flow rate and pressure in the post-injector components (column and detector) drop to zero rapidly. Pressure in the pre-injector components (pump and connecting lines) rises rapidly, since the pump keeps delivering solvent to the dead-ended injector inlet port. When flow is reestablished at the end of the transition period, a pressure surge travels down the post-injector components. These transients cause many detectors to produce baseline disturbances, since they are somewhat flow sensitive. Also, the transients, if they are large enough, cause column efficiency to deteriorate, because the transients change the packing geometry of the stationary phase particles.

The rate of the pre-injector pressure rise during the transition period depends on the flow rate, pre-injector fluid volume, fluid compressibility, and mechanical compliance. The magnitude of the rise depends on the time duration of the flow interruption. Similarly, the magnitude of the pressure shock to the column and detector depends on the duration of the flow interrupt. The period of interruption of prior non-bypass injectors, when used with typical pre and post-injector components and typical flow rates, is large enough to cause measurable loss of efficiency over a period of time. Although any one injection (transient) event usually causes only a small efficiency loss, the cumulative effect of many injections results in a serious shortening of useful column lifetime, due to a continuously degrading efficiency.

An injector which avoided significant dilution of sample with solvent, while also avoiding significant interruptions in flow of liquid into the column, would improve the performance of the chromatographic system without sacrificing column lifetime.

SUMMARY OF THE INVENTION

In accordance with one embodiment of the present invention, an injector is provided for injecting a sample into a chromatographic column, or the like, which enables operation with minimal dilution of the sample with mobile phase liquid, while also enabling operation with minimal interruption of flow into the column. The injector includes rotor and stator elements that can rotate relative to one another between load and inject positions, and which have an interface. A first of the elements has a pump port through which high pressures liquid is pumped, a column port leading to the column, a pair of sample ports which connect to a sample loop, and a vent port, with all ports having openings at the interface. The second element has a pair of channels, with a first channel connecting pump and column openings in the load position, and connecting the column opening and a first-sample opening in the load position. The pump and column openings are closely spaced, by a small angle of less than 10°, so that the interruption time, during which there is neither mobile phase liquid nor sample liquid being pumped into the column, lasts only long enough for the rotor to turn by an even smaller angle of less than 10°.

In one injector, the first channel, which connects the adjacent pump and column openings, extends by a large angle beyond the pump opening. Accordingly, the rotor turns by a large angle between the load and inject positions, where the angle is several times greater than the angle between the pump and column openings. By providing a large extending portion of the first channel, the port and column openings continue to be connected throughout most of the rotation angle of the rotor. Only as the end of rotation is approached does the trailing edge of the first channel disconnect from the pump opening and the leading edge of the channel connect to the first-sample opening. When the rotor element is rapidly turned, there is only a very brief interruption of flow. Although the pump opening lies only a small distance from the column opening, there is essentially no flow between them, even if there is a scratch in the interface that permits such flow, because both openings are at about the same high pressure.

The novel features of the invention are set forth with particularity in the appended claims. The invention will be best understood from the following description when read in conjunction with the accompanying drawings.

BRIEF DESCRIPTION OF THE DRAWINGS

FIG. 4 is a rear elevation view of the injector of FIG. 2, also shown in the load position.

FIG. 5 is a rear elevation view of the injector of FIG. 3, also shown in the inject position.

FIG. 6 is a view of the injector of FIG. 4, shown in a transition position between the load and inject positions.

FIG. 7 is a view similar to that of FIG. 6, but at a later transition position.

FIG. 8 is an enlarged view similar to FIG. 7, but at a later transition position.

FIG. 9 is a rear elevation view of a modification of the injector of FIG. 4, shown in the load position.

FIG. 10 is a view similar to that of FIG. 9, but showing the injector in the inject position.

FIG. 11 is an enlarged view similar to that of FIG. 9, but showing the injector in a transition position.

FIG. 12 is a simplified front view of an injector constructed in accordance with another embodiment of the invention, shown in the load position.

FIG. 13 is a view similar to that of FIG. 12, but showing the injector in a transition position between the load and inject positions.

FIG. 14 is a view similar to that of FIG. 13, but showing the injector in the inject position.

FIG. 15 is an exploded rear perspective view of the injector of FIG. 12, shown in the load position.

FIG. 16 is a simplified rear view of an injector constructed in accordance with another embodiment of the invention, shown in the load position.

FIG. 17 is a view similar to FIG. 16, but showing the injector in the inject position.

FIG. 18 is a simplified view of an injector constructed in accordance with another embodiment of the invention, shown in a load position.

FIG. 19 is a view similar to that of FIG. 18, but showing the injector in the inject position.

DESCRIPTION OF THE PREFERRED EMBODIMENTS

Figure 1:
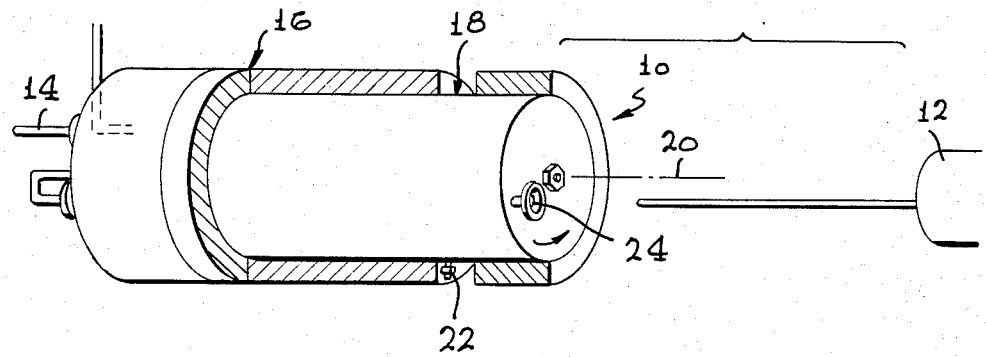
FIG. 1 is a front perspective and partially sectional view of an injector constructed in accordance with the present invention.

FIG. 1 illustrates a sample injector 10 of the present invention, which can receive a small sample from a microsyringe 12 or other loading device and deliver the sample from a column outlet 14 to a chromatographic column or other analytical device. The injector includes a stator element or stator 16, and a rotor element or rotor 18 that can pivot about an axis 20. Stops 22 limit the rotor to pivoting by about 60° (in different but similar models the angle ranges from 45° to 90°) between a load position at which a sample is loaded through a sample-receiving port 24 into the injector, and an inject position at which the sample is injected under high pressure into the column.

Figure 2:
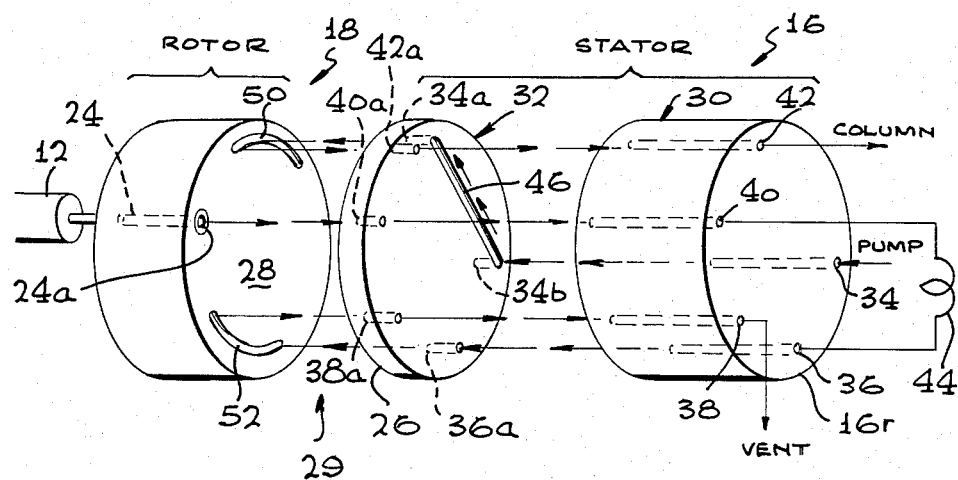
FIG. 2 is a rear end, perspective, and exploded, simplified view of the injector of FIG. 1, shown in the load position.
Figure 3:
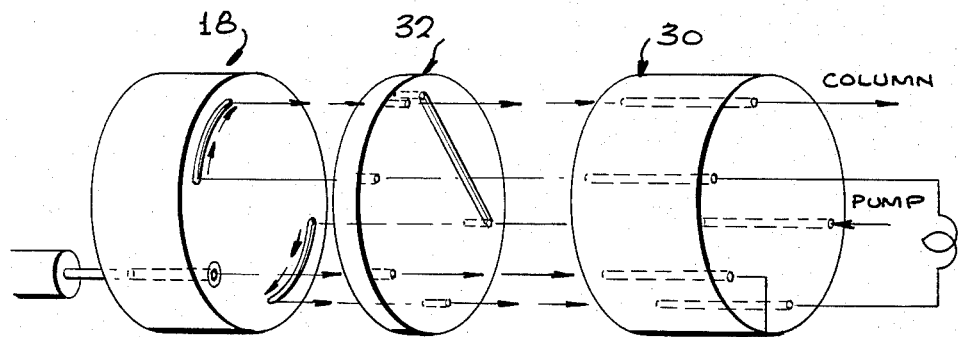
FIG. 3 is a view similar to that of FIG. 2, but showing the injector in the inject position.

As shown in FIG. 2, which is a rear view instead of the front one of FIG. 1, the stator and rotor have adjacent faces 26, 28 that form an interface 29 between the stator and rotor. The stator 16 is constructed with two parts 30, 32 for ease of manufacture, but these parts are fastened together. The rearward end 16r of the stator provides access to five passages or ports 34–42 that extend from the rear end 16r to the interface 29. One port 34 receives a mobile phase liquid from a pump that delivers fluid at a high pressure, such as 5,000 psi (a typical range is 500 to 7000 psi). Another port 42 leads to the chromatographic column, into which fluid must be injected at a high pressure. Another port 38 is connected to a venting device through which fluid can be discharged and usually discarded. Two other ports, 40, 36, are sample ports which are connected to a sample loop 44 that temporarily holds much of the sample that is to be injected into the column. (The sample loop could be built into the stator housing as a "loop" in the form of a chamber or passage that connects the two sample ports).

Four of the ports 36–42 have single openings 36a–42a at the interface. The pump port 34 has two openings 34a, 34b at the interface, that are connected together by a pump passage 46 that is formed in one of the stator parts 32. The rotor 18 includes the single sample-receiving port 24 with an opening 24a at the interface, and also forms a pair of passages or channels 50, 52 in the rotor face 28, for selectively connecting some of the stator port openings.

To analyze a sample originally contained in the syringe 12, the syringe is operated to pump the sample at substantially atmospheric pressure into the sample loop 44. Solvent previously filling the sample loop is discharged through the vent port 38. At the same time, mobile phase fluid is pumped under high pressure into the pump port 34 and out of the column port 42, for the purpose of maintaining a continous flow into the column. As best shown in FIG. 4, the route taken by the sample is through the sample receiving port to its interface opening 24a, through the first sample opening 40a and its port and into the sample loop 44. Solvent already in the sample loop passes out of it through the second sample port and its opening 36a, through the second channel 52, and through the vent opening 38a and the vent port into a venting container (not shown). At the same time, solvent pumped under high pressure into the pump port 34, passes through it and through the pump channel 46 to the first pump opening 34a at the interface. This high pressure solvent then enters the first channel 50 and moves through it to the column opening 42a, and through the column port into the chromatographic column. It should be noted that the channels 50, 52 are shown as having a width greater than the diameter of the port openings such as 34a, 42a etc., only to facilitate illustration; they are preferably the same.

When the sample has been loaded into the sample loop 44, that sample can be injected into the column. This is accomplished by first rotating the rotor in the direction of arrow I by an angle such as 60°, to the inject position shown in FIG. 5. Such rotation moves the two channels 50, 52 to the positions shown in FIG. 5. In this position, high pressure fluid flowing into the pump port 34, flows to the pump opening 34b at the interface, and from there through the second channel 52 to the second sample port 36 into the sample loop 44. The high pressure fluid flowing through the sample loop pumps sample liquid out of the other end of the loop and through the first sample port 40 and out of its opening 40a, to flow through the first channel 50 into the column port 42. The sample flows from there into the column where it can be analyzed. It should be noted that the first pump opening 34a is now deadended at the interface, and while it applies high pressure solvent liquid to the interface, there is no flow out of the pump opening at 34a. Thus, the device avoids creation of two parallel fluid streams, and therefore avoids dilution of the sample as it flows to the column.

The injector is constructed to avoid an important problem that has arisen in prior art injectors of this type. During rotation of the rotor from the load position of FIG. 4, and in the direction of arrow I to the inject position of FIG. 5, there is an interruption of flow of fluid into the column. Such interruption in flow has disadvantages. As discussed earlier in "Background of the Invention", one disadvantage is that it can cause disturbance in the baseline of the chromatographic detector. Another is that it can cause deterioration of column efficiency, leading to a decrease of resolution of the components of the injected sample. The greater the magnitude of the flow transient, the greater the undesireable effects. The placement of the first pump outlet 34a very close to the column port opening 42a, minimizes the duration of such interruption in flow, and reduces the problems of detector baseline noise and column efficiency deterioration to a negligible level.

When the injector is in the load position of FIG. 4 and the rotor begins to turn in the direction of arrow I, the first channel 50 continues to connect the first pump opening 34a and column opening 42a, to maintain a continuous flow into the column. When the rotor has rotated most of the way towards the inject position, the injector will assume a transition position shown in FIG. 6, wherein the rotor has turned by an angle A. The trailing edge 50t of the first channel still lies behind the pump opening 34a, so the pump and channel openings 34a, 42a continue to be connected to continue high pressure flow into the column. When the rotor turns slightly more, to the position shown in FIG. 7, the trailing edge 50t of the channel has passed completely by the pump opening 34a, so the pump no longer pumps directly into the channel. However, the channel 50 has still not turned far enough for the leading or forward edge 50f to reach the first sample opening 40a. At this time, in the position shown in FIG. 7, there is an interruption in flow into the column, which can have adverse affects if continued for a significant period of time. As the rotor continues to turn toward the inject position, it reaches the position shown in FIG. 5, wherein the leading edge 50f of the first channel is connected to the first sample opening 40a, so that high pressure fluid flow into the column can begin again, with the first fluid passing through the channel 50 being solvent and the following fluid being the sample liquid.

The angle M (FIG. 4) between the first pump opening 34a and the column opening 42a is small, to minimize the time during which there is an interruption of flow into the column opening 42a. For example, where the total angle p that the rotor turns in moving between the load and inject positions is 60°, the angle m may be 10° or less. The small angular rotation during which flow to the column is interrupted is smaller than the angle m, since there is an even smaller angle r (FIG. 8) of rotation between disconnection of the first pump opening 34a and connection of the first-sample opening 40a and also of the second pump opening 34b. The briefness of interruption of flow to the column is obtained by constructing the first channel 50 so it extends a considerable angle n (FIG. 8) behind the first pump opening 34a, and locating the leading edge 52f of the second channel so it connects to the second pump opening 34b after a small angle of rotation r past the position at which the first channel 50 disconnects from the first pump opening 34a. For example, while the total angular rotation p of the rotor between the load and inject positions may be 60°, the angle r of rotation required to begin flow into the column opening may be less than one-tenth as much such as less than 6°. If it takes one-tenth second to turn the rotor from the load position to the inject position, then the interrupt time when no fluid passes towards the column may be less than one-tenth as much, or less than one-hundredth second.

The geometry of the injector such as is shown in FIG. 8 also minimizes the possibility of significant leakage of solvent along with the sample into the column. The closeness of the pump opening 34a to the column opening 42a could lead to the possibility of leakage of sample liquid or solvent liquid between them, since liquid pumped into the column is at a high pressure, such as 5,000 psi, and it is possible for a scratch to be accidently made in the interface surfaces. However, during the inject position as in FIG. 5, both the column opening 42a and pump opening 34a are at about the same high pressure, so that even if there is a scratch in the interface surface between them, a negligible amount of fluid will flow between them.

In one example of an injector, as shown in FIG. 8, the openings such as 34a and 42a lay on a circle of rotation having a radius R such as 0.1 inch from the axis of rotation 20. Each of the openings has a diameter d of 10 mil (1 mil equals one-thousandth inch). The openings or holes are separated by a distance e of 20 mils, and the angle m between adjacent edges of the hole 34a, 42a is about 10°. The minimum separation e that can be used depends on the materials of which the injector is constructed and on the pressures used. The angle r of rotor movement between disconnection of the trailing edge 50t from the hole 34a, and the connection of the leading edge 52f of the other channel with pump hole 34b, is only 5°. If it requires one-tenth second to rotate the rotor by 60°, then it requires only about 8 milliseconds to rotate by the angle r of about 5° during which flow to the column is interrupted. The time actually can be briefer, in that for manual and certain power drives, the rotor will initially turn more slowly as it first accelerates in rotation, and can be turning very rapidly during the last part of its rotation as it approaches the inject position.

FIGS. 9–11 show another injector 160 which is somewhat similar to that of FIG. 4, except that the openings and channels are arranged in a somewhat different manner, to avoid dead space in the load position, as in the portion of the channel 50 in FIG. 4 that extends by the angle n. Dead space, in which liquid is opened to a flowing stream but in which liquid does not flow with the stream, is undesireable because mobile phase liquid, or solvent, can accumulate in the dead space during a period when liquid is being pumped directly from the pump port to the column. If the solvent is changed, then some of the old solvent will remain in the dead space, and may be injected into the column when the rotor is turned. This produces an "artifact", or contaminent, when fluid is injected into the column during the inject position. In the apparatus of FIGS. 9–11, such dead space is avoided during the load condition of FIG. 9, by rearranging the two interface openings 162a, 162b of the pump port 162, and by repositioning the rotor channels 164, 166. In particular, the pump openings are located so that one pump opening 162b is located at an end of the channel 164 which is opposite the end which is adjacent to the column port opening 168. The other pump opening 162a lies between them. Solvent flows through both openings 162a, 162b into the channel 164 in the load position.

The injector of FIGS. 9–11 is also constructed to produce no interruption in flow during operation of the injector. The interface openings and channels are arranged so that at the transition position of FIG. 11, the pump port 162 is connected to both channels 164, 166. Thus, as the trailing channel end 164t is breaking connection with the pump port 162a, high pressure fluid has already begun to be applied through another route (via channel 166, second-sample port 170, loop 172 and first-sample port 174) to channel 164 and to the column port 168.

In one injector that has been designed as shown in FIG. 11, the channels and opening were positioned so that at the indicated transition position the trailing edge 164t of one channel overlapped the pump opening 162a by d/4, where d is the diameter of each opening. At the same time, the leading edge 166f of the other channel 166 had already overlapped the other pump opening 162b by d/4. The separation between the pump port opening 162a and the column port opening at 168 was d/2, and the angle t between them was about 3°. At the instant shown in FIG. 11, the same pressure is applied to both ends of the sample loop 172, so there is virtually no flow through it. In both the load and inject positions, virtually the same pressure is applied to the column and pump openings, so their closeness does not lead to leakage between them.

The injector of FIGS. 9–11 can be constructed with a greater separation between the column port opening 168 and the adjacent pump opening 162a, such as about twice the hole diameter d. This avoids the creation of a very narrow wall between these openings. This also results in a brief interruption in flow.

FIG. 15 illustrates another injector 84 which has a pump port 86 with two openings 86a, 86b at the stator-rotor interface that are connected by a passage 90. This injector is also shown in FIGS. 12–14, which are front rather than rear views of the injector 84. When the rotor is in the load position of FIG. 12, high pressure solvent can flow through both pump openings 86a, 86b through a rotor channel 92 to a column opening 94. At the same time, a sample is injected through a first sample opening 96 to fill or partially fill a sample loop 98, with the flow passing through a second-sample opening 100 and through a second channel 102 to a vent opening 104. When the rotor is turned in the inject direction indicated by arrow I, and reaches the inject position of FIG. 14, one of the pump openings 86a is connected through the channel 102 to the second sample opening 100 to pump the sample from the loop through the first sample opening 96 and through the channel 92 to the column opening 94. No fluid passes out of the other pump opening 86b. FIG. 13 shows a transition position in which the channel 92 is about to break connection with the pump opening 86b and make connection with the first sample opening 96, and wherein the other channel 102 is approaching the pump opening 86a. It may be noted that a second (optional) vent opening 106 is provided in this injector to provide a passageway for liquid used to flush the sample inlet port.

FIG. 16 shows still another injector 110, in which the various openings at the interface are closely spaced. The stator has five ports, each with one opening at the interface, including a pump opening 112 for receiving high pressure solvent, a column opening 114 for delivering fluid to a chromatograhic column, a first sample opening 116 connected to one end of a sample loop 118, a second sample opening 120 connected to the other end of the loop, and a vent opening 122. The rotor has a sample-receiving port 124 with an opening at the interface for delivering sample liquid, and a pair of channels 126, 128. The injector is shown in the load position wherein fluid from the pump opening 112 flows directly to the column opening 114. When the rotor is turned a small amount in the inject direction indicated by arrow I, the rotor assumes the position shown in FIG. 17, wherein fluid from the pump opening 112 passes through the sample loop and the channel 128 to the column opening 114.

In the injector of FIG. 17, all interface openings on the stator are spaced apart by an angle D which is less than one-sixth the usual 60° rotation, or in other words less than 10°. This produces a small interruption time. However, the interruption time in the apparatus of FIG. 16 may be somewhat greater than that for the apparatus of FIG. 4, since it may require a short period to accelerate the rotor to a rapid rotation speed, so the average rotation rate in FIG. 16 may not be as great as the rotation rate at the very end of rotation in the injector of FIG. 4. The injector 110 in the inject position shown in FIG. 17, also avoids leakage between the pump and column openings 112, 114, in the inject position, even though the openings are very close together, since both are under high pressure. However, there can be some leakage between the vent opening 122 and either of the sample openings 120 or 116 because they are so close together. There also could be leakage between passage 128 and ports 124, 116 in the load position.

FIGS. 18 and 19 show another injector 130, of the "plug type", which operates on the same principle as the injector of FIGS. 12–15, but wherein the interface 132 between the rotor 134 and stator 136 is cylindrical. The sample insert port 148 is located in the stator and connected through a rotor channel 146 to a sample port 144. The other sample port 142 is connected through another channel 140 to the vent port 138. The pump and column ports 150, 152 are connected through another channel 154. It can be seen that the opening 150a at the interface has two ends at 156 and 158 that are separated by most of the angle of rotation of the rotor between the load and inject positions.

Thus, the invention provides a sample injector which has the advantage of non-bypass injectors of avoiding dilution of the sample with mobile phase liquid from the pump, and which also provides substantially the same advantage obtained in a bypass loop injector of avoiding significant interruptions in flow into the column. This can be accomplished by locating column and pump openings at the interface between the rotor and stator, so they are close together, with a separation angle of less than 10°. The other port openings at the interface may be widely spaced to avoid leakage between them, so the rotor must turn much more than 10° between the load and inject positions. Close spacing of a pump and column opening can be achieved by providing a channel in the rotor, that connects the pump and column openings in the load position, so the channel extends by a considerable angle away from the pump opening and can maintain connection between pump and column openings through most of the rotor rotation toward the inject position. A pair of pump openings at the interface can be provided that are spaced apart by most of the angle of rotation of the rotor in moving between the load and inject positions. While the injector has been described for use with a mobile phase that is a liquid, it can be used with any fluid including a gas, a liquid, and a super-critical liquid.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. In an injector which includes a rotor that can pivot between load and inject positions about an axis and that has a sample-receive port for receiving a sample, and which also includes a stator with pump, column, first-sample, vent, and second-sample ports, and with the rotor having first and second channels at the rotor-stator interface, each channel having leading and trailing edges, the first channel connecting the pump and column ports at the load position and connecting the column and first-sample ports at the inject position, and the second channel connecting the second-sample and vent ports in the load position and coupling the second-sample port to the pump port in the inject position, the improvement wherein:

said pump port includes a pump inlet spaced from said stator-rotor interface, first and second spaced pump openings in said stator at the stator-rotor interface, and a conduit in said stator which connects said pump inlet to said first and second pump openings;

said column port has an opening at the stator-rotor interface and said first pump opening has an edge that lies at an angle of less than 10° about said axis from the nearest edge of said column opening, said second pump opening is spaced by more than twice said angle from said first pump opening, and said second channel is positioned so that in the inject position said second channel connects the second-sample opening to said second pump opening; and said second channel is positioned so that at a transition position at which the trailing edge of the first channel breaks connection with said pump port, during rotor pivoting toward the inject position, the leading edge of the second channel lies within 10° of connection with the pump port.

2. The improvement described in claim 1 wherein:
said channels are positioned so that in the load position, said column opening lies at one end of said first channel, said second pump opening lies at the opposite end of said first channel, and said first pump opening lies between them and in connection with said first channel.

3. In an injector which includes a rotor that can pivot between load and inject positions about an axis and that has a sample-receive port for receiving a sample, and which also includes a stator with pump, column, first-sample, vent, and second-sample ports, and with the rotor having first and second channels at the rotor-stator interface, each channel having leading and trailing edges, the first channel connecting the pump and column ports at the load position and connecting the column and first-sample ports at the inject position, and the second channel connecting the second-sample and vent ports in the load position and coupling the second-sample port to the pump port in the inject position, the improvement wherein:

said channels are positioned so that at a transition position at which the trailing edge of said first channel breaks connection with said pump port during rotor pivoting toward the inject position, the leading edge of said second channel is already connected to said pump port.

4. The improvement described in claim 3 wherein:
said pump port has first and second pump openings at the rotor-stator interface, and said pump openings are spaced apart by more than 10° and are positioned so that at said transition position the trailing edge of said first channel just breaks connection with said first pump opening and the leading edge of said second channel has made connection with only a portion of said second pump port.

5. An injector comprising:
stator and rotor elements which can rotate relative to one another angularly about an axis of rotation between predetermined load and inject positions, and which have adjacent interface surfaces;

a first of said elements having a pump port for receiving a mobile phase fluid high pressure, a column port for delivering fluid to a chromatography column, first and second sample ports for connection to opposite ends of a sample loop, and a vent port for venting fluid, each port having at least one opening at the interface between the elements;

a second of said elements having a sample-receive port for receiving a sample fluid, said second element also having first and second largely circumferentially-extending channels in its face;

said openings positioned with the opening of said second-sample port lying angularly between a pump opening and the opening at said vent port, and said second channel positioned so in said load position said second channel extends between said second-sample and vent openings, and in said inject position said second channel extends between said second-sample opening and a pump opening;

said column opening lying angularly between a pump opening and said first-sample opening, and in the load position said first channel extends between a pump opening and said column opening, and in the inject position said first channel extends between said column opening and first-sample opening;

said pump port has two angularly-spaced pump openings at the interface surface of said first element, including a first pump opening positioned so it opens to said first channel and is connected therethrough to said column opening in the load position, but does not open to either channel in the inject position, and a second pump opening positioned so it opens to said second channel and is connected therethrough to said second-sample opening in the inject position.

6. The injector described in claim 5 wherein:
said second pump opening is positioned so it lies at an end of said first channel in the load position, and lies at an end of said second channel in the inject position.

7. An injector comprising:
stator and rotor elements which can rotate relative to one another angularly about an axis of rotation between predetermined load and inject positions, and which have adjacent interface surfaces;

a first of said elements having a pump port for receiving a mobile phase fluid under high pressure, a column port for delivering fluid to a chromatography column, first and second sample ports for connection to opposite ends of a sample loop, and a vent port for venting fluid, each port having at least one opening at the interface between the elements;

a second of said elements having a sample-receive port for receiving a sample fluid, said second element also having first and second largely circumferentially-extending channels in its face;

said openings positioned with the opening of said second-sample port lying angularly between a pump opening and the opening at said vent port, and said second channel positioned so in said load position said second channel extends between said second-sample and vent openings, and in said inject position said second channel extends between said second-sample opening and a pump opening;

said column opening lying angularly between a pump opening and said first-sample opening, and said first channel is positioned so in the load position said first channel extends between a pump opening and said column opening, and in the inject position said first channel extends between said column opening and first-sample opening;

said channels each have leading and trailing edges, said channels are positioned so that at a predetermined transition position between the load and inject positions, the trailing edge of said first channel and the leading edge of said second channel are each partially connected to the pump port.

8. A method for using an injection device having stator and rotor elements that lie adjacent at an interface, to transfer a sample fluid from a container to an analyzing apparatus such a chromatographic column at high pressure, comprising:

placing said rotor element in a load position and loading said device, including pumping said sample fluid at low pressure from said container through a port of a first of said elements to an interface between said elements, through a first-sample port of a second of said elements, through a sample loop, through a second-sample port of said second element to said interface, and through a second channel in said second element;

said step of loading also includes pumping a solvent fluid from a high pressure pump through a pump port of said second element to said interface, through a first channel in said first element and from said first channel to a column port of said first element that is connected to an analyzing apparatus;

turning said rotor element to an inject position and at said inject position pumping said solvent at high pressure from said pump port, through said second channel, through said second-sample port and said loop to said first sample port, and through said first channel to said column port, to said analyzing apparatus;

said pump port has two spaced pump openings at said interface, and said step of turning includes disconnecting a first of said pump openings from said first channel and connecting said second channel to a second of said pump openings, all within 10° of rotation of said rotor.

9. The method described in claim 8 wherein:

said step of turning includes at least partially connecting said second channel to said pump port before completely disconnecting said first channel from said pump port.

* * * * *